US00PP15907P3

(12) United States Plant Patent
Davidson

(10) Patent No.: US PP15,907 P3
(45) Date of Patent: Aug. 2, 2005

(54) HYBRID TEA ROSE PLANT NAMED 'HADDEL'

(50) Latin Name: *Rosa hybrida*
Varietal Denomination: Haddel

(76) Inventor: Harvey Daniel Davidson, 3 El Verano Rd., Orinda, CA (US) 94563

( * ) Notice: Subject to any disclaimer, the term of this patent is extended or adjusted under 35 U.S.C. 154(b) by 145 days.

(21) Appl. No.: 10/724,476

(22) Filed: Dec. 1, 2003

(65) Prior Publication Data

US 2005/0120445 P1 Jun. 2, 2005

(51) Int. Cl.[7] ..... A01H 5/00

(52) U.S. Cl. ..... Plt./130

(58) Field of Search ..... Plt./130, 132, 135, Plt./137

*Primary Examiner*—Howard J. Locker

(57) ABSTRACT

A new and distinct rose cultivar of the Hybrid Tea class characterized by: having stems without prickles; large peach shaded flowers; flowers borne one to the stem; rapid repeat blooms; on upright bushy plants.

1 Drawing Sheet

Botanical/commercial classification: *Rosa hybrida*/Hybrid Tea Rose Plant.

The present invention relates to a new and distinctive cultivar of rose plant of the Hybrid Tea class, which was originated by my crossing an unnamed yellow seedling as the seed parent with 'Smooth Sailing' as the pollen parent. The cultivar name of this plant is designated as 'Haddell'. It is being marketed under the commercial name of 'Smooth Delight'.

Among the novel characteristics possessed by the new cultivar which distinguish it from:

(a) All other cultivars of which I am aware are:

(1) Prickles being absent from any stems.

(2) Large peach shaded flower.

(3) Single flower to the stem.

(4) Very consistent free bloomer.

(5) Upright bushy plant.

(b) Seed parent: Unnamed yellow hybrid tea seedling; few prickles. Pollen parent: Tall growing; cream flowers; no prickles. Asexual reproduction of the new rose cultivar by budding onto the rootstock 'Dr. Huey', as performed at Wasco, Calif., shows that the aforementioned and all other distinctive characteristics come true to form and are established and transmitted through succeeding propagations.

The accompanying drawing shows typical specimens of the vegetative growth and flowers of the new cultivar in different stages of development and as depicted in color as nearly true as it is reasonably possible to make the same in a color illustration of this character.

The following is a detailed description of my new cultivar, with color terminology in accordance with The Royal Horticultural Society Colour Chart (R.H.S.C.C.). The terminology used in the color description herein refers to plate numbers such as 'Yellow Group 16A' found in Fan 1 of The Royal Horticultural Society Colour Chart.

Parentage:

*Seed parent.*—Unnamed yellow seedling, hybrid tea.

*Pollen parent.*—'Smooth Sailing', hybrid tea. Registered (IRAR). Not patented.

The following observations are made of specimens grown outdoors in Orinda, Contra Costa County, Calif., in the month of October, 2003.

FLOWER

Blooming habit:

A. Bud:

(*1*) *Size.*—Sepals enclosed, 28–32 mm from base of sepals to top of bud.

(*2*) *Form.*—Ovoid.

(*3*) *Sepals.*—34–40 mm in length; 6 to 8 m extension beyond bud; no serration shown on sepal edges. Generally 3 out of 5 sepals show appendages on each side, 2 to 5 mm length. Sepals show light glandular development on edges and outer surface. Heavy cotton matting on inner surface, fine matting on outer surface. Outside color: near to Yellow Green Grp. 146B with shadings of Greyed Orange Grp. 176A; Inside: Greyed Green Grp. 195A.

(*4*) *Peduncle.*—Length — 6½ to 7 cm. Surface: smooth; a few glandular hairs; no prickles. Strength: firm. Color: near Yellow Green 146D; with shades of Greyed Orange Group 176D.

(*5*) *Receptacle.*—Shape: Oblong, 13–16 mm diameter; Color: same as peduncle.

(*6*) *Color.*—When sepals first divide, outside bud petals with shadings of Red Group 47B, C, D and shades near to Yellow Orange Grp. 23D.

B. Bloom:

(*1*) *Size.*—When open: 11–12 cm.

(*2*) *Borne.*—One flower per stem.

(*3*) *Form.*—Globular.

(*4*) *Petalage.*—Average — 34 to 36.

(*5*) *Color.*—Early open: outside petals near to Red Group 56C; inner petals near to Orange Group 26C and D with shades of Yellow Orange Group 22C. Aging petals: Outer petals: near to Red Group 36C and D; inner petals: near to Yellow Orange 22C.

C. Petals:
(1) *Texture.*—Firm.
(2) *Appearance.*—Flexed.
(3) *Form.*—Symmetrically spaced.
(4) *Arrangement.*—Regular.
(5) *Petaloids in center.*—Average 6 to 8.
(6) *Persistance.*—Petals hold well; petals drop cleanly at end of bloom.
(7) *Fragrance.*—Slight.
(8) *Lasting quality.*—On bush about 6–7 days; as cut flower about 4–6 days.

REPRODUCTIVE ORGANS

A. Stamen:
(1) *Arrangement.*—Regular around styles.
(2) *Number.*—Average: 170–180.
(3) *Length—Average:* 5 to 10 mm from base.
(4) *Filaments.*—Color: Close to Red Group 47C.
(5) *Anthers.*—Color: Yellow Orange Grp. 21C.
(6) *Pollen.*—Color: Yellow Orange Group 21C.

B. Pistil:
(1) *Styles.*—Length: 8–16 mm from center of ovary; number 130–140; color: near to Red Grp. 51B; sparsely coated with white hairs.
(2) *Stigma.*—Color — Close to Yellow Grp. 12B.
(3) *Ovary.*—Shape — oblong; 9–10 mm center cross section at sepal base.

C. Hips: Does not set seed.

PLANT

A. Form: Upright.
B. Growth: Height: average 1.25 m; Width: average 0.75 m.
C. Stem length: Basal break to flower bud tip: average 1–1.25 m.
D. Foliage: Compound of 3 to 5 leaflets on bloom stem; 5 to 7 leaflets on main canes.
(1) *Quantity.*—Stems well covered.
(2) *Color.*—New foliage: Upper side near to Greyed Orange 177B; under side near Greyed Orange 177C; areas of Yellow Green 147B. Old foliage: upper side near to Yellow Green 147A; under side near to Yellow Green 147B.
(3) *Shape.*—Mature 5 leaflet: Length: stipule base to tip of leaflet — 11–13 cm. Center end leaflet: Oval and pointed. Length: 5–6 cm; Width: 4–4½ cm.
(4) *Texture.*—Firm, leathery, gloss finish.
(5) *Edge.*—Serration on outer edge: Average 4–5 points per 1 cm, with ½ to 1 mm peak.
(6) *Rachis.*—Few glandular hairs on lower and upper side. No prickles on lower side.
(7) *Stipules.*—Length 18–20 mm; auricle 4–5 mm. Edge of stipule to tip of auricle with many glandular hairs.

E. Resistance to disease: Powdery mildew, rust and black-spot: Good.
F. Wood:
*New wood.*—Color close to Yellow Green 146C; shadings near to Greyed Orange Group 176D; Bark — smooth.
*Old wood.*—Color close to Yellow Green 147B; Bark — smooth.
G. Prickles: None.
H. Winter hardiness: Average.

I claim:

1. A new and distinct rose cultivar of the hybrid tea class, characterized in particular by prickles being absent from any stems, large peach shaded flowers which are borne singly, consistent and free blooming, with the plant being upright, bushy and of medium height, substantially as herein shown and described.

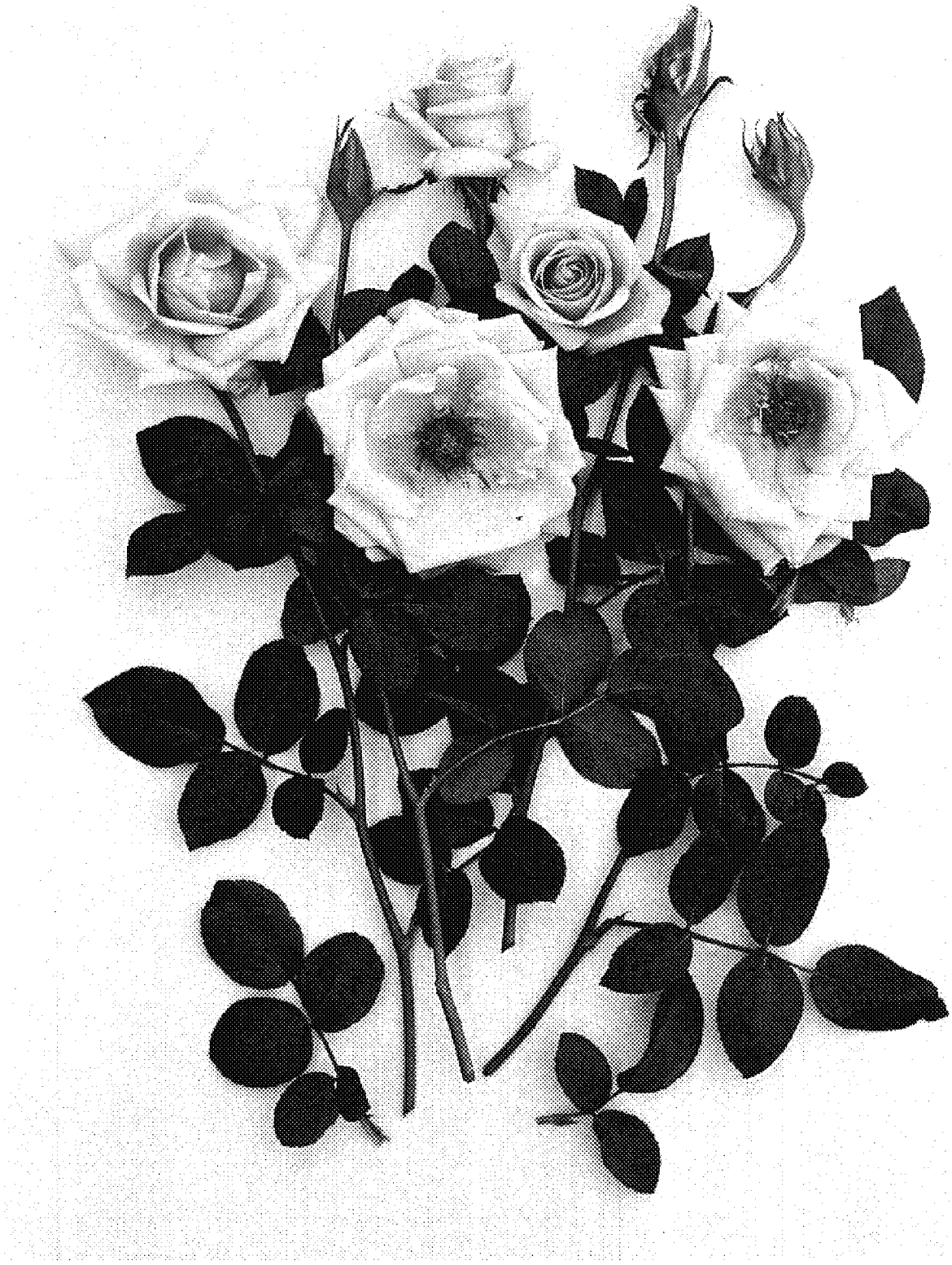

* * * * *